(12) United States Patent
Nueesch

(10) Patent No.: US 8,142,392 B2
(45) Date of Patent: Mar. 27, 2012

(54) MILK PUMP

(75) Inventor: Hansueli Nueesch, Remetschwil (CH)

(73) Assignee: Trimed AG, Triesen (CH)

( * ) Notice: Subject to any disclaimer, the term of this patent is extended or adjusted under 35 U.S.C. 154(b) by 1030 days.

(21) Appl. No.: 11/705,419

(22) Filed: Feb. 13, 2007

(65) Prior Publication Data
US 2007/0191763 A1 Aug. 16, 2007

(30) Foreign Application Priority Data

Feb. 13, 2006 (DE) .......................... 10 2006 006 417
Jun. 9, 2006 (CH) ......................................... 0938/06

(51) Int. Cl.
*A61M 1/06* (2006.01)
(52) U.S. Cl. ........................................................ 604/74
(58) Field of Classification Search ...................... 604/19
See application file for complete search history.

(56) References Cited

U.S. PATENT DOCUMENTS

| | | | |
|---|---|---|---|
| 37,677 A | 2/1863 | Colvin | |
| 50,457 A | 10/1865 | Colvin | |
| 331,952 A | 12/1885 | Durand | |
| 2,060,063 A | 11/1936 | Frimand | |
| 4,411,603 A | 10/1983 | Kell | |
| 4,583,970 A | 4/1986 | Kirschner | |
| 4,813,932 A | 3/1989 | Hobbs | |
| 5,358,476 A | 10/1994 | Wilson | |
| 5,749,850 A | 5/1998 | Williams et al. | |
| 6,110,141 A * | 8/2000 | Nuesch | 604/74 |
| 6,749,582 B2 * | 6/2004 | Britto et al. | 604/74 |
| 2002/0072702 A1 | 6/2002 | Quay | |
| 2007/0078383 A1 | 4/2007 | Tashiro et al. | |

FOREIGN PATENT DOCUMENTS

| | | |
|---|---|---|
| DE | 729 251 | 12/1942 |
| DE | 82 14 315 U1 | 9/1982 |
| EP | 0 000 339 A1 | 1/1979 |
| EP | 0 123 269 B1 | 10/1984 |
| EP | 0 385 933 A2 | 9/1990 |
| EP | 0 733 376 B1 | 9/1996 |
| EP | 1 231 955 B1 | 8/2002 |

(Continued)

OTHER PUBLICATIONS

European Search Report Application/Patent No. 07101346.0-2310 dated May 30, 2007.

*Primary Examiner* — Nicholas Lucchesi
*Assistant Examiner* — Jason Flick
(74) *Attorney, Agent, or Firm* — Buchanan Ingersoll & Rooney PC

(57) ABSTRACT

A milk pump for pumping milk from a woman's breast, includes a receptacle for receiving milk pumped from the woman's breast and a manual pumping unit. The pumping unit includes a displacement space surrounded by a wall that defines a longitudinal axis and having a predetermined cross-sectional dimension. This displacement space is or may be connected to a breast hood. The pump unit includes a suction member which is displaceable within displacement space substantially along its longitudinal axis. The suction member is formed as a generally cup-shaped membrane so that a first portion of said cup-shaped membrane extends transversely to the longitudinal axis of said displacement space, whereas a second portion extends substantially in circumferential direction. The membrane is able to move substantially free of friction relative to a wall of the displacement space.

21 Claims, 6 Drawing Sheets

FOREIGN PATENT DOCUMENTS

| | | |
|---|---|---|
| GB | 2 166 353 A | 5/1986 |
| WO | 92/00111 A1 | 1/1992 |
| WO | 95/18639 A1 | 7/1995 |
| WO | WO 03/013628 | 2/2003 |
| WO | 2004/058330 A1 | 7/2004 |
| WO | 2006/000292 A1 | 1/2006 |
| WO | WO 2006/117352 | 11/2006 |
| WO | WO 2007/017968 | 2/2007 |

* cited by examiner

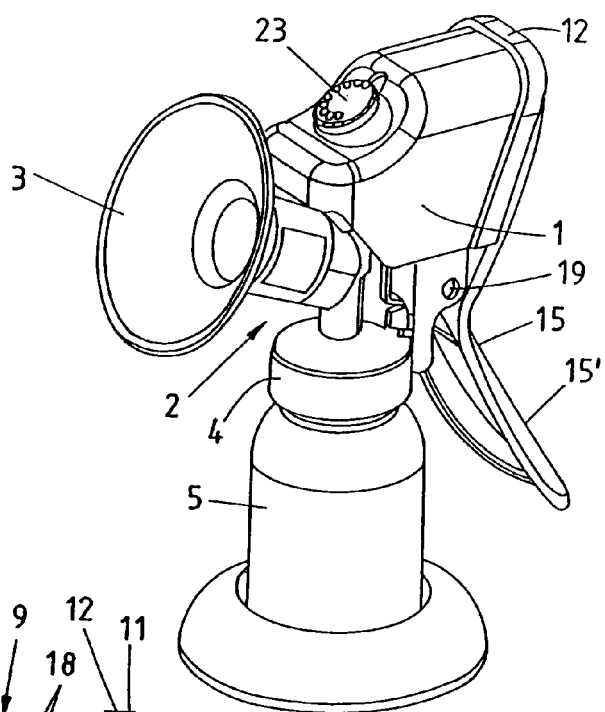
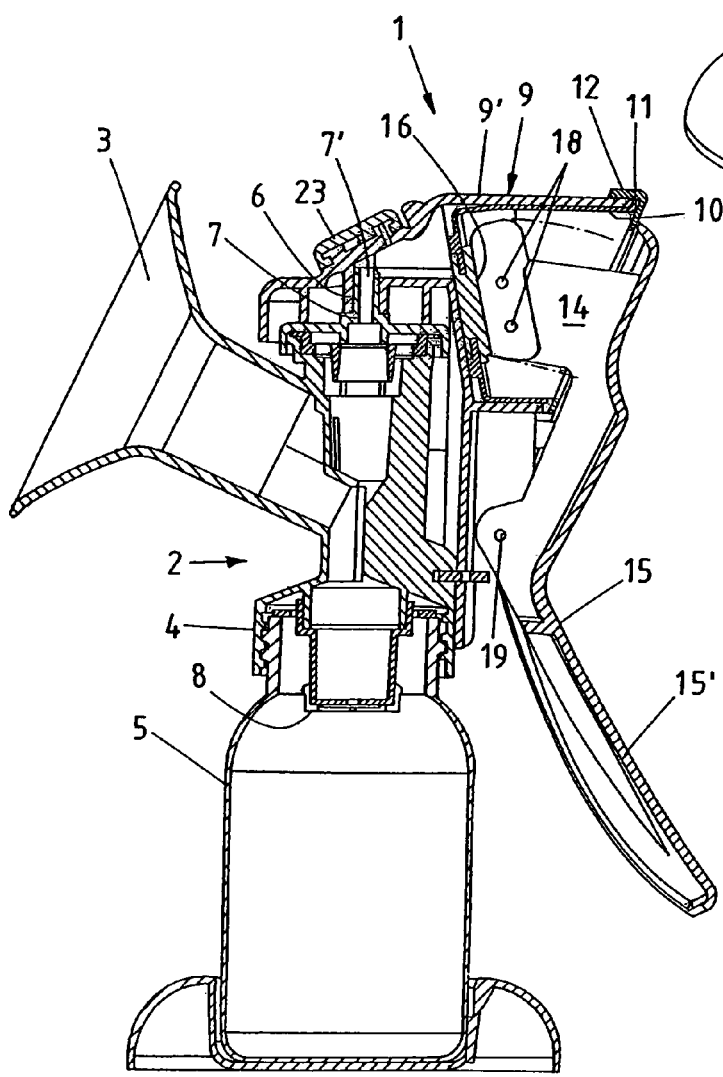

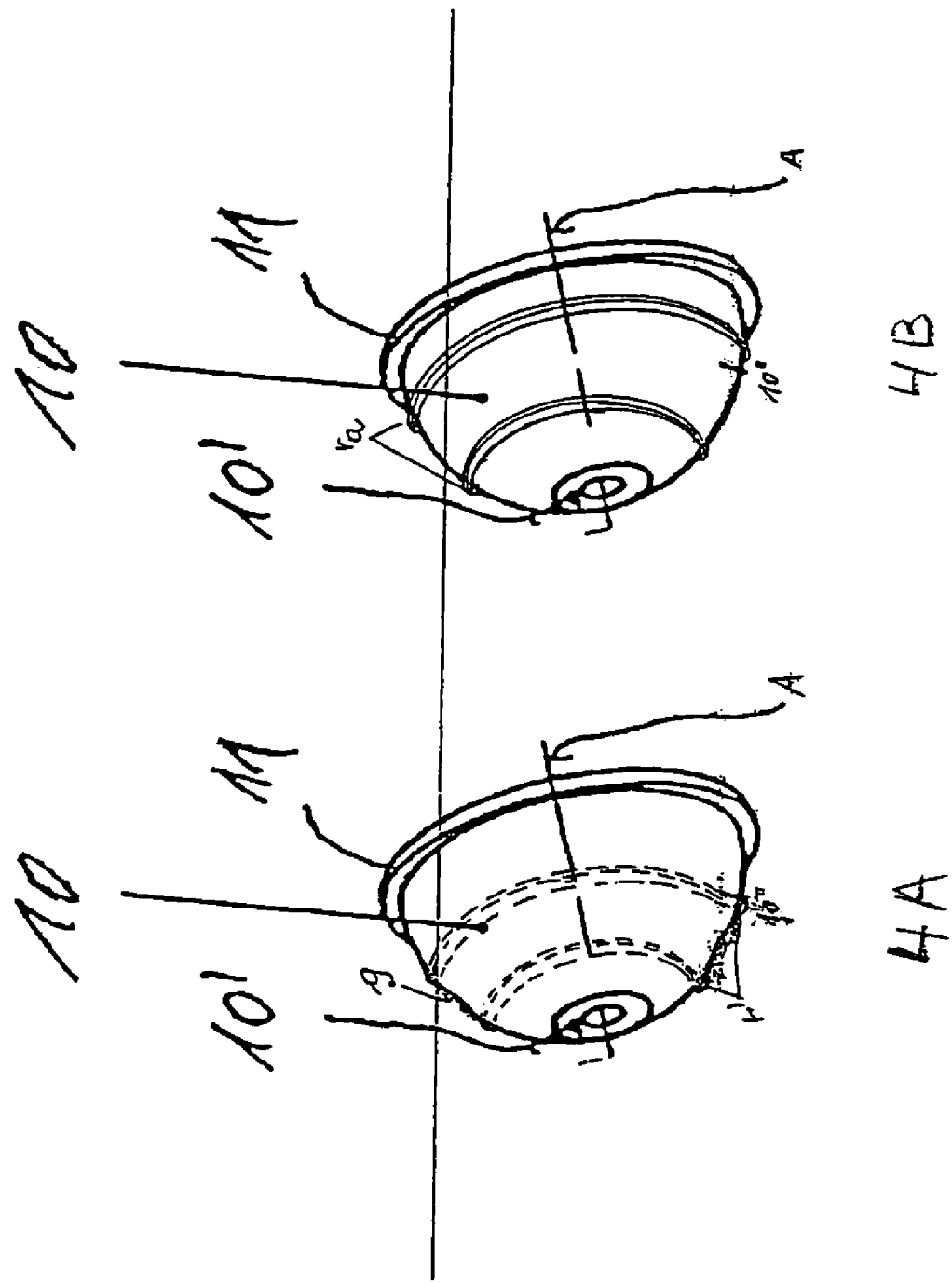

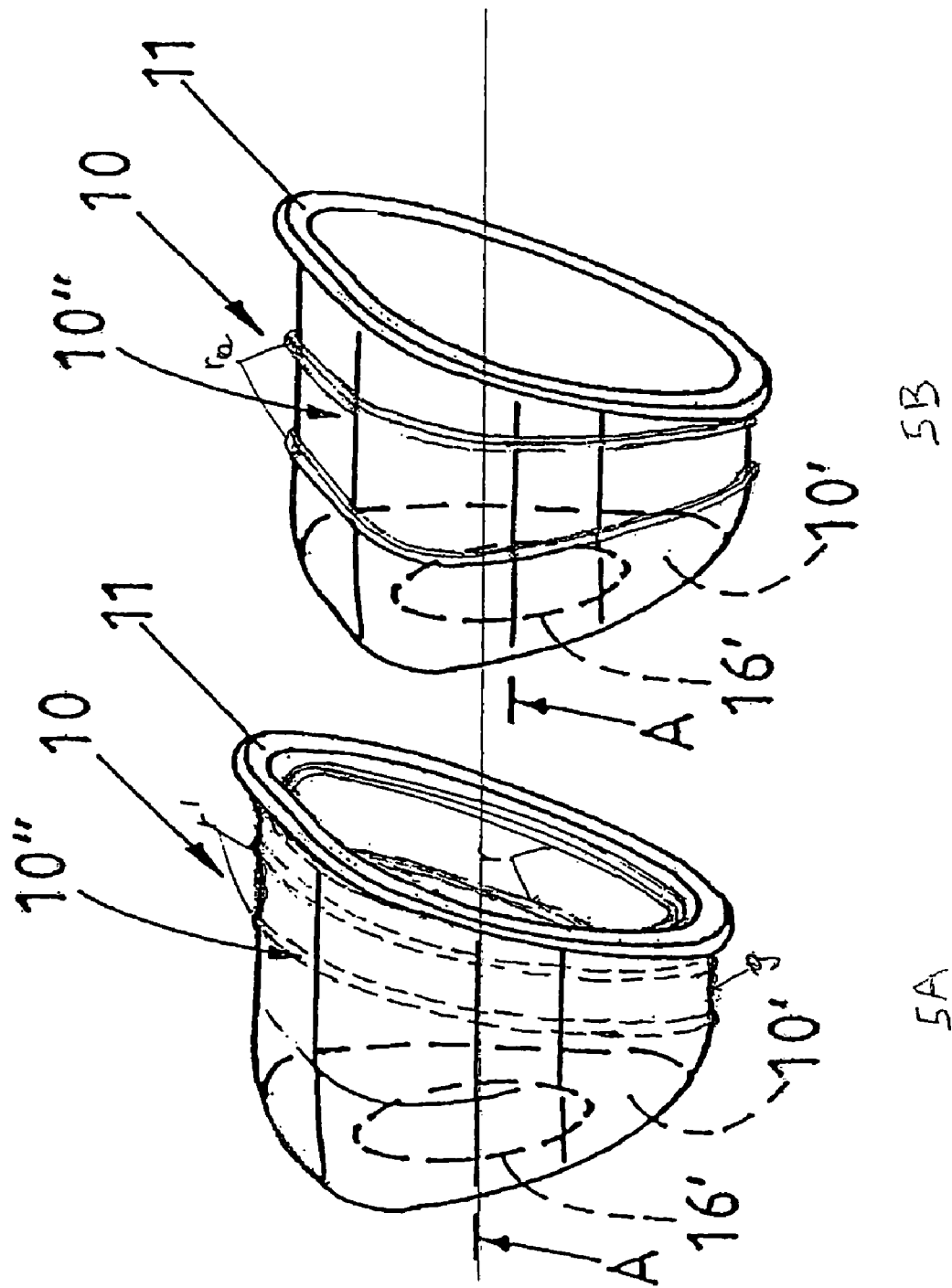

MILK PUMP

RELATED APPLICATIONS

The present application claims priority under 35 U.S.C. §119 to German Application No. 10 2006 006417.8 filed Feb. 13, 2006 and to Swiss Application No. 00938/06 filed Jun. 9, 2006, the contents of which are hereby incorporated by reference in their entireties.

FIELD

A milk pump is disclosed which includes, for example, a manual pumping unit above an opening that leads to a receptacle.

BACKGROUND

Milk pumps are known, for example, from U.S. Pat. No. 4,813,932, on the one hand, and from EP-1 231 955, on the other hand. In both cases, a piston within the displacement space is moved by an actuation lever. In particular, working mothers pump mother milk in this way in order to be able to put it at the disposal of the baby during day time, while the child is under the care of a foster-mother or of a relative.

It is known that working mothers are subjected to considerable stress. Pumping mother milk takes a certain time which even intensifies the morning stress situation. Although manual pumps of the above described type are relative economical in price, many women do without them and often choose a more expensive motor pump. As a reason, often the quick fatigue of the hand is stated.

Such fatigue will particularly occur, if the pump is of a short-stroke type so that many pumping movements are necessary in order to achieve a sufficient suction effect. This applies in particular to designs having a relative short membrane, such as the rolling membrane, that seals a piston, according to WO 2004/058330 or according to EP-0 733 376 where the stroke is quite limited so that they have to be actuated more often to achieve the same result as, for example, a piston pump. Moreover, such membranes are quite sensitive to tension and are easily susceptible to fissures, because they are generally moved against their inherent elasticity.

Since overflowing of milk into the pumping space should be prevented, it has also become known (see WO 2006/000292) to insert a membrane over the whole suction cross-section, and to move this membrane indirectly by a piston and its suction effect. However, such design is quite space consuming and has, furthermore, the disadvantage that the piston motion has to be synchronous with the movement of the membrane; for example, if the membrane, when being inserted into the pump (e.g., after washing it after use), is inserted in a somewhat squeezed, and thus shortened way, whereas the piston executes its full length first stroke, an efficient and easy pumping work can no longer be performed.

SUMMARY

A milk pump is disclosed which includes a manual pumping unit above an opening that leads to a receptacle. The unit comprises a displacement space substantially surrounded by at least one wall, communicating or being able to communicate with a breast hood, and defining a longitudinal axis. The unit comprises also a suction member that is moveable to and fro in that space by means of, for example, a manual, actuation device, such as a lever (e.g., a two-armed lever), which is pivotally supported in a middle region. A restoring device can be provided for the actuation device for returning it into a predetermined starting position.

The longitudinal axis does not mean that the displacement space has to be elongated. It means merely that this axis can extend along a certain dimension of the displacement space, the dimension extending along the direction of displacement of the suction member. Exemplary embodiments can address the fatigue of the hand, and to provide measures against fatigue.

When investigating a certain number of such manual pumps and similar ones, it has been determined that a good part of the energy introduced by hand is absorbed by the friction of the piston along the wall of the displacement space. It is clear that the pumping piston has to be sealed against the wall along its circumference, if one wants to prevent losing part of the suction effect which, in turn, would result in an increased pumping energy being required.

In the course of this investigation, however, another reason why actuation of a pumping piston may be made more difficult was discovered: Even relatively small tolerances in shaping the displacement space or mechanically or thermally caused deformations can make actuation considerably more difficult. Although this applies to a smaller extent to linear displacement spaces, which have a straight longitudinal axis, such as in the above-mentioned U.S. Pat. No. 4,813,932, with such a design a greater resistance will result from the friction of an actuation catch along an actuation surface connected to the piston. This friction occurs because the actuation lever executes a pivotal movement which, however, due to the linear displacement space has to be transformed into a linear motion.

EP 1 231 955 discloses a vaulted displacement space which, in some sense, is the enveloping surface of the piston movement. But in this case, a problem is aggravated: apart from the fact that removing the injection molded part from the mold is made more difficult, this design involves an increased precision, because in the case where the center of the vault does not coincide exactly with the center of the vaulted piston movement, an increased friction of the piston packing along the wall of the displacement space will result which impedes greatly actuation of the milk pump. However, such a divergence may occur for a variety of reasons: by unavoidable tolerance in injection molding, by mechanical or thermal influences or stresses, as well as simply by wear. The increased friction caused in this way can lead to a quicker fatigue of the pumping hand.

Fatigue could easily be avoided, if a motor pump is used instead of a manual pump. Motors, in general, have to be overdimensioned anyway in order to overcome such tolerances easily. In this case, one is not confronted with this problem. However, such motor pumps involve a greater investment which, considering the mostly short lived demand, is not worth doing.

A milk pump is disclosed whose actuation causes less fatigue. In an exemplary embodiment, a suction member is formed by a generally cup-shaped membrane which, inside the displacement space, is also moveable towards the wall and has a portion, which extends substantially transversely to the displacement space, and is moveable without friction to and fro by the manual actuation device.

As has already been mentioned above, membranes have been applied fro milk pumps in various shapes. For example, DE-C-729 251, DE-U-82 14 315 or EP-0 000 339 suggest the use of a balloon-shaped membrane as a pumping element which is not accommodated within a displacement space. However, such pumping balloons may be actuated with difficulty.

WO 92/00111 discloses a mucus extractor where a thumb actuated expansion bellows having plies is employed. Such expansion bellows have to have plies and tapers which confer a certain elasticity. The pumping volume is, therefore, quite limited. This does not create problems for a mucus remover, because there will ordinarily be a little amount of mucus to be pumped. However, in milk pumps, such an expansion bellow requires more pumping movements to obtain virtually the same result as with a piston pump. Moreover, the maintained stress on the thumb causes also fatigue.

In contrast, a cup-shaped membrane as disclosed herein can minimize friction, because a piston packing sliding over a wall is not provided, and the membrane has such a free space within the displacement space that it may even be moved towards the wall. Because the membrane comprises not only a portion that extends transversely to the displacement space, but also a portion that extends in peripheral direction of the wall, which means that it is cup-shaped, a relatively large pumping stroke can be enabled so that pumping milk can be performed quickly without any pain or trouble.

The actuation device can be a two-armed lever supported in its middle region, because this type of actuation device is mechanically simple and, moreover, facilitates pumping by reducing the necessary force due to the lever transmission.

A restoring spring for returning the actuation device into a predetermined starting position can be provided. Such a feature is not necessary because it would be possible to provide actuation holes for putting a finger through, similar as with scissors (see the hole 58 in WO 95/18639) and to do without a restoring device which, in turn, may be formed in any fashion known per se. This function can alternately be performed by the cup-shaped membrane itself, as will be described later.

An exemplary stroke movement of the membrane is enabled, if the membrane is about pot-shaped having a bottom surface and at least one circumferential surface. Just such a membrane, but also any other suitable one, can be suitably guided in its movement. To this end, a guiding part, connected to the lever, can be fastened to the center region of that portion, which extends transversely to the displacement space. A disk-shaped, guiding part can be suitably smaller relative to the smallest transversal dimension of the displacement space by, for example, at least 15%, preferably by at least 20%, particularly at least 30%, being for example smaller by about 35%, so that a frictional resistance is securely avoided.

The displacement space can comprise a straight longitudinal axis and/or a straight wall which, in some cases, starting from the region of the opening to the receptacle, diverges. In this way, removal from the injection mold can be facilitated. Moreover, as will become apparent from the following description, some space can be provided in which the membrane or its guiding part may move exerting a transversal component of movement (for example if an arched movement of the membrane, e.g. by a pivoting lever, is caused, while the displacement space extends substantially linearly), without causing friction losses which could result in fatigue of the pumping hand.

According to a further exemplary embodiment, the displacement space comprises a cross-section that deviates from a cylindrical or circular cross-section. It could be an oval cross-section, for example, particularly one where the oval has a substantially vertical longer oval axis. This latter embodiment can be particularly advantageous, if the displacement space has a straight, linear axis, and the guiding part for the membrane exerts a pivotal movement. However, an embodiment having an about four-cornered cross-section, e.g. with rounded corners, can be used as well.

A particularly simple and cost effective construction can be obtained if the cup-shaped membrane is at least approximately in the shape of a spherical cap, thus forming also the restoring device by its shape. In principle, this restoring device can include a spring (in addition), but this will be, in general, not necessary. In any case, this construction will result in a different suction effect over the actuation stroke of the actuation device, but this will not be detrimental for simplified embodiments of the pump.

In such a case, the displacement space itself can comprise a shape which is about in the form of a spherical cap which receives the membrane of an approximately complementary shape. In practice the curvature of the spherical caps will advantageously be of the same dimension so that they supplement each other and a good suction effect is ensured.

BRIEF DESCRIPTION OF THE DRAWINGS

Further details will become apparent from the following description of preferred embodiments schematically illustrated in the drawings, in which FIG. 1 is a perspective view of a milk pump according to an exemplary embodiment;

FIG. 2 is a vertical cross-section of the pump according to FIG. 1;

FIGS. 4A and 4B are schematics of a membrane according to exemplary embodiments; and FIGS. 5A and 5B are schematics of a membrane according to exemplary embodiments.

DETAILED DESCRIPTION

Figure 1A:
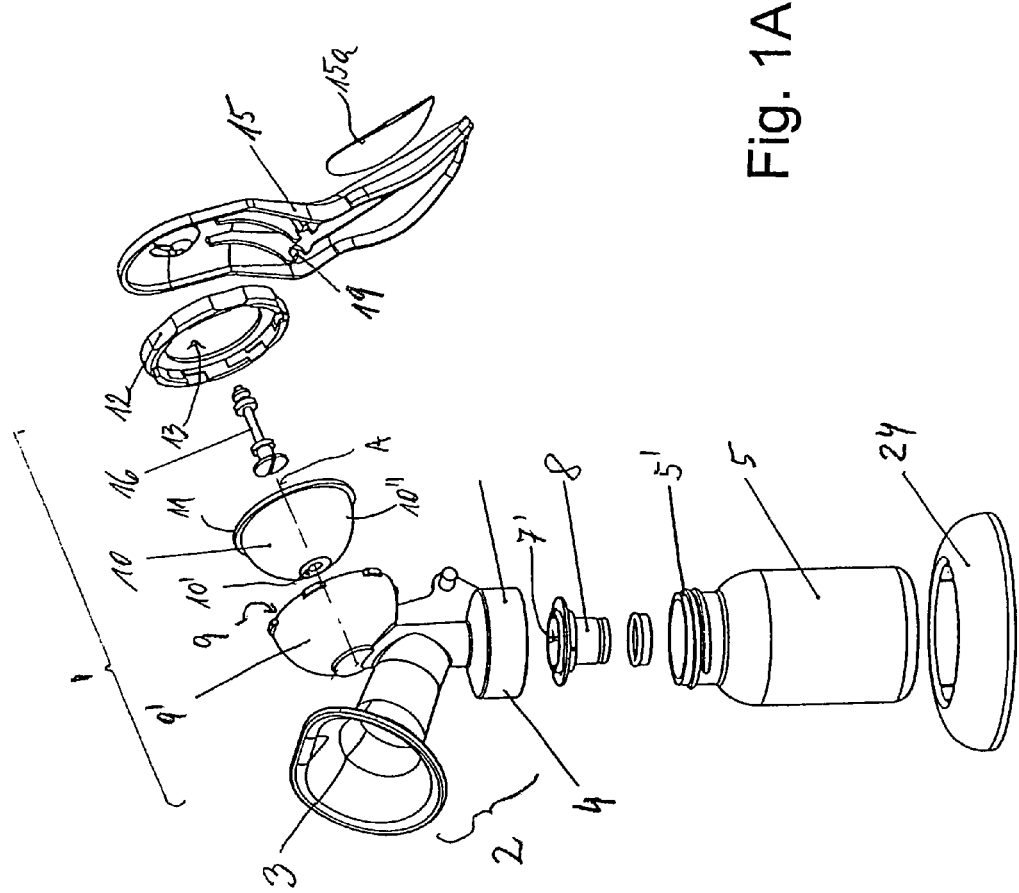
FIG. 1A is an exploded representation similar to that of FIG. 3 of an embodiment of the milk pump showing the displacement space and the parts which cooperate with it.

The milk pump illustrated in FIGS. 1 and 2 comprises an upper part 1 (manual pumping unit) which (at 6, 7, at a connecting opening 7') is plugged onto an interconnection part 2. The interconnection part 2 comprises a breast hood 3 or horn, on the one hand, and a screwing portion 4 by which the pump unit may be screwed onto a milk collection receptacle 5. Between the milk collection receptacle 5 and the interconnection part 2 is a non-return valve 8 (FIG. 2), as is known per se. A regulation knob 23 may be provided at the upper side for controlling the amount of secondary air supplied and, thus, the effort in actuating the pump. A suitable, exemplary control is described, for example, in U.S. Pat. Nos. 6,042,560 and 6,290,671 the contents of which are incorporated herein by reference in their entirety.

Figure 3:
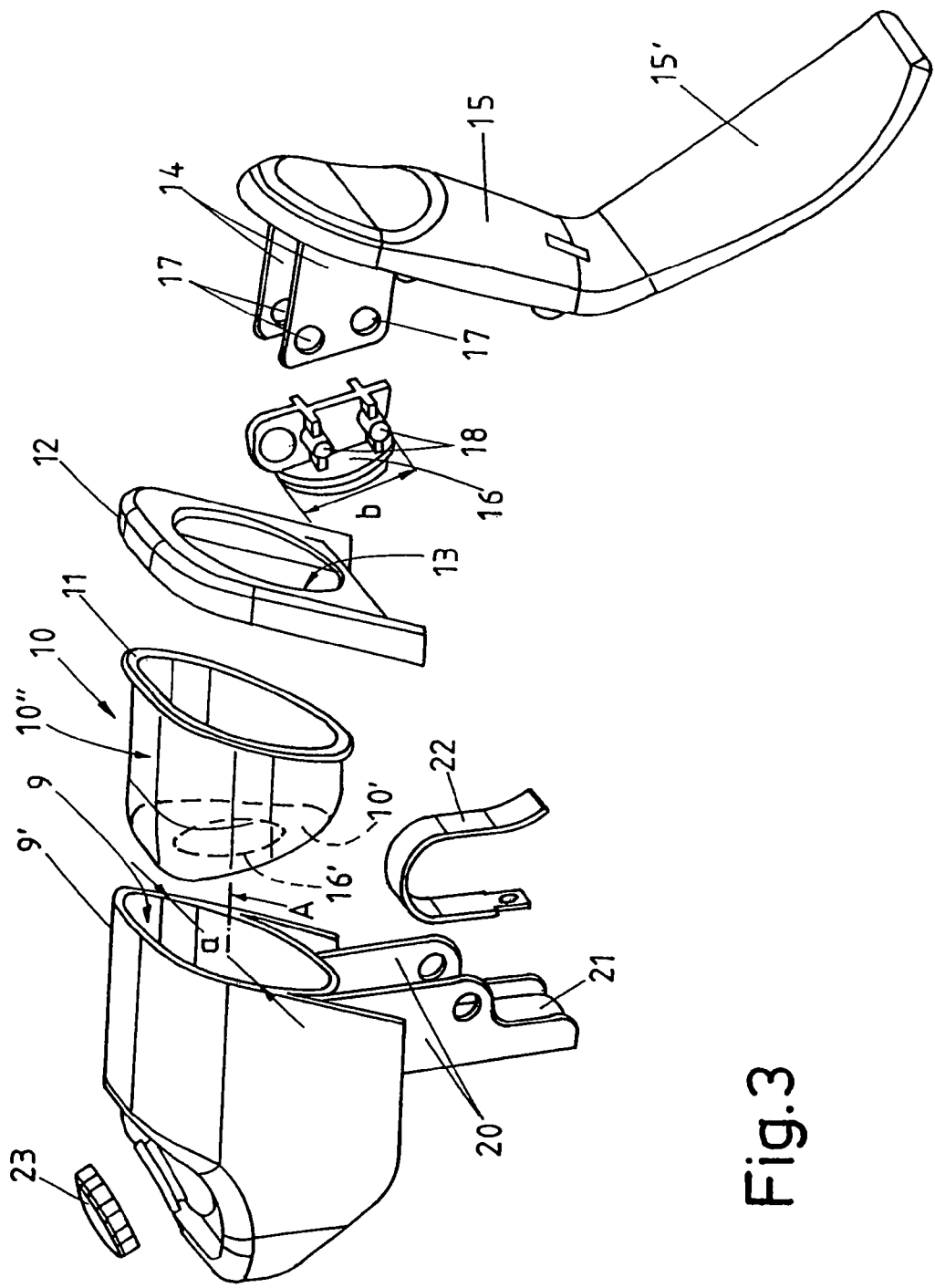
FIG. 3 is an exploded view of an exemplary displacement space and the parts accommodated therein.

Within the upper part 1 is a displacement space 9, as seen in FIG. 3, which is surrounded by a wall 9'. The wall 9', as seen in FIG. 3, has a substantially four-cornered cross-section with rounded corners. An about cup-shaped membrane 10 is inserted into this displacement space 9, and its border 11 is fastened to a frame 12 at one end of the wall 9' which delimits the displacement space 9.

The frame 12 has a passage opening 13 through which an about disk-shaped guiding shield 16 mounted on two projections 14 of a two-armed lever 15 is provided. To this end, the projections 14, according to FIG. 3, comprise holes 17 into which pins or projections 18 on the guiding shield 16 may be inserted and/or snapped in.

FIG. 2 illustrates in dash-dotted lines the movement of the guiding shield 16 to which the about cup-shaped membrane 10 is fastened. To this end, the membrane 10 comprises a portion 10' (in dotted lines in FIG. 2) which extends transversely to the displacement space 9 and comprises an opening 16', that receives the guiding shield 16 (see FIGS. 2 and 3), as well as a circumferentially of the wall 9 extending portion 10" when the membrane 10 extends in full length through the displacement space 9 (see FIGS. 2, 3). Thus, the portion 10', as it were, forms the bottom surface of the cup-shaped membrane 10, whereas the portion 10" forms the (at least one) circumferential surface.

Since the displacement space 9 has a linearly extending axis A, whereas the guiding shield 16 is connected to the lever 15 to pivot with it about a pivoting axis 19 (FIGS. 1, 2), a movement in the sense of the dash-dotted lines (as may be seen in FIG. 2), when the lower end of the lever 15 is pressed. This causes a small motion of the shield 16 away from the wall 9' at the upper side of the displacement space 9, but causes an approach towards the lower side. This means that the membrane 10 is also moveable towards and away from the wall 9'. But even in the case of a coincidence of the axis of movement of the guiding shield 16 and the longitudinal axis A (i.e. either both are curved, or both are straight linear), the difference between the transversal dimension of the guiding shield 16 to the inside width of the displacement space 9 is such that a movement of the membrane 10 towards the wall can be at least possible. In this sense, it may be understood when in this context it is spoken of a portion 10' that may move towards the wall 9'.

In order to enable such a transversal movement of the guiding shield relative to the wall 9', the transversal dimension b of the, e.g., disk-shaped, guiding part 16 is smaller by, for example, at least 15%, preferably by at least 20%, particularly by at least 30%, for example by about 35% than the minimum transversal dimension a (FIG. 3) of the displacement space 9. This leaves space enough for moving the membrane 10 and avoids or minimizes any risk which could make actuation of the membrane 10 difficult when moving to and fro within the displacement space 9.

A ring for slipping a finger through it (or a bow for several fingers) at the lower actuation end 15' of the lever 15 can be included. In such an embodiment, a restoring device can be eliminated if desired. A restoring spring, simply formed as a leaf spring 22 can be provided between two holding cheeks 20 which props against a transversal wall 21, whereas its end facing the lever 15 props against this lever. In this way, the lever and the membrane is always returned into a predetermined starting position, and the operator has only to press the end 15' to actuate the membrane 10, i.e. to contract it or to stretch it.

Figure 2A:
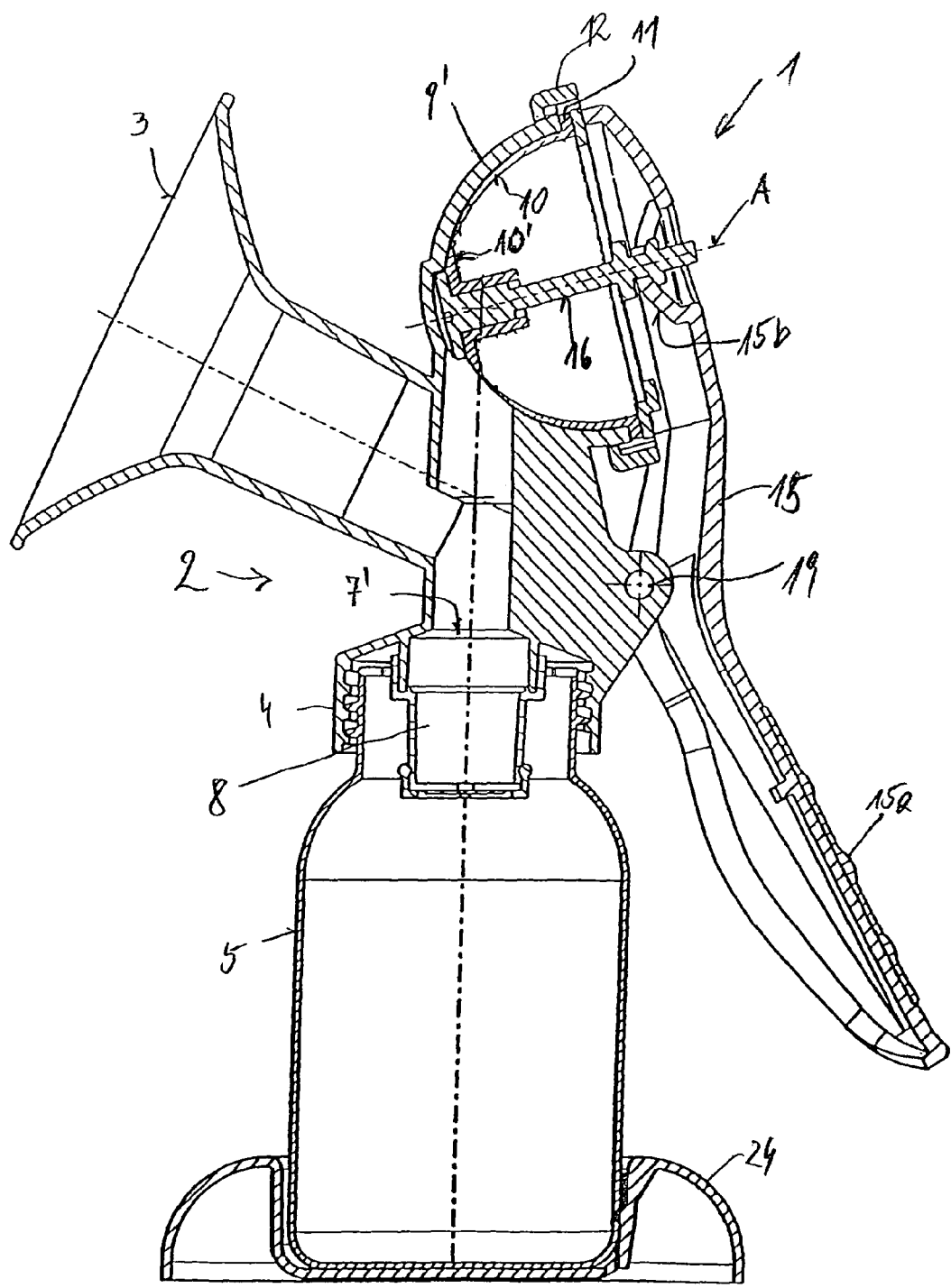
FIG. 2A is a longitudinal cross-section of the assembled milk pump according to FIG. 1A.

The milk pump represented in FIGS. 1A and 2A together with its milk receptacle 5 stands suitably on a foot piece 24 which enlarges its floor space. Within the upper part 1, a displacement space 9 is provided again, which is surrounded by a wall 9'. The wall 9', in this case, can have a substantially spherical cap shape. Into this displacement space 9 an exemplary, complementarily shaped, membrane of elastic material in the shape of a spherical cap can be inserted and fastened to a frame 12 that holds its border 11 at one end of the wall 9' which delimits one end of the displacement space 9. In this case, the curvature of the displacement space 9 and of the membrane 10 with respect to circumference, curvature and axial length in the direction of axis A can have the same dimensions.

On the other hand, FIG. 2A shows clearly that the thickness of the membrane 10, in correspondence with an exemplary embodiment, varies in axial direction (axis A). In this way, the spring characteristic exerted by the membrane 10 may be influenced, but on the other hand uniform folding of the membrane when actuating the lever arm 15a can be ensured due to the fact that the smallest thickness is in the center region 10', and the largest thickness is in the region of the border 11. This variation in thickness could also be made in steps, or can be continuous, as is represented in FIG. 2A. Other variations in thickness can be used, for example by providing rings and/or grooves which extend around the axis A. Of course, it would also be possible to provide the approximately pot-shaped membrane of FIGS. 1 to 3 with different thicknesses, rings or grooves, as shown in FIGS. 4A, 4B, 5A and 5B.

The frame 12, here again, comprises a through opening 13 through which an about pin-shaped guiding part 16 mounted on a two-armed lever 15 is provided, which is pivoted about an axis 19 and has a handle surface 15a, the free end of the guide part 16 being connected to the center portion 10' (FIG. 2) which extends transversely to the displacement space 9 and its axis A. The guide part 16 can be secured to a holding surface 15b of the lever 15 in a way so that it may easily be detached if desired.

At least when the membrane is stretched (released), as in FIGS. 1A and 2A, a portion 10" joining their portion 10' extends about in circumferential direction of the wall 9'. In this way, movement of the membrane 10 towards the wall 9' and away from it is possible. In any case, the guide part 16 at the place of fastening at the center portion 10' is considerably smaller than the minimum transversal dimension of the displacement space 9. This leaves space for displacing the membrane 10 and avoids any friction which could render the actuation of the membrane 10 difficult, when displaced to and fro within the displacement space 9. As may be seen from FIGS. 1A and 2A, the curvature of the membrane 10 and of the wall 9' is about equally dimensioned (when neglecting that the membrane's curvature has to be a little bit smaller to fit into the hollow spherical cap of the wall 9').

As mentioned above, if a ring for slipping a finger through it (or a bow for several fingers) were provided at the lower actuation end 15' of the lever 15, a restoring device can be more easily avoided. For example, the membrane 10 can have an inherent elasticity and tend to keep its spherical cap shape, and thereby act as a restoring device so that a special device for this purpose is not necessary.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A milk pump for pumping milk from a woman's breast, comprising: a milk collector for receiving milk pumped from said woman's breast; a manual pumping unit which includes: a wall forming and surrounding a displacement space, said displacement space defining a longitudinal axis and having a predetermined cross-sectional dimension; a connector for connecting said displacement space to a breast hood; a suction unit displaceable in said displacement space formed by the wall, substantially along said longitudinal axis, said suction unit being formed as a membrane; and an actuator for mechanically displacing said membrane substantially in an axial direction, wherein the suction unit includes a circumferential outer edge border portion at one end which is fixed to the wall, a bottom portion extending substantially transversely to the longitudinal axis at another end and an extending portion extending between the border portion and the bottom portion, the extending portion varying in thickness in a direction along the longitudinal axis, said variations providing a spring characteristic and being formed as a plurality of grooves and/or rings, said extending portion being able to move substantially free of friction relative to said wall.

2. Milk pump as claimed in claim 1, wherein said actuator comprise a lever of predetermined length.

3. Milk pump as claimed in claim 2, wherein said lever is a two-armed lever, pivotally supported in a middle region of its length.

4. Milk pump as claimed in claim 1, comprising:
a spring acting onto said actuator for restoring the actuator in a predetermined initial position.

5. Milk pump as claimed in claim 1, wherein said longitudinal axis is straight.

6. Milk pump as claimed in claim 1, wherein said wall is straight.

7. Milk pump as claimed in claim 1, wherein said wall diverges in a direction away from said milk collector.

8. Milk pump as claimed in claim 1, wherein said displacement space has a cross-section transverse to said longitudinal axis which deviates from a circular cross-section.

9. Milk pump as claimed in claim 8, wherein said displacement space has a four-cornered cross-section with rounded corners.

10. The milk pump as claimed in claim 1, wherein said actuator comprises a lever detachably connected to said membrane.

11. A milk pump as claimed in claim 1, wherein said suction unit being formed as a membrane having an open rim.

12. Milk pump as claimed in claim 11, wherein the transition from said first portion to said rim is continuous.

13. Milk pump as claimed in claim 1, wherein said suction unit is cup-shaped.

14. Milk pump as claimed in claim 13,
wherein said manual pumping unit includes a guide connected to said lever and being fastened to a center region of said first portion of said cup-shaped membrane.

15. Milk pump as claimed in claim 14, wherein said guide is substantially disk-shaped having a predetermined disk dimension in transverse direction to said longitudinal axis, said disk dimension being smaller than the minimum cross-sectional dimension of said displacement space by at least 15%.

16. Milk pump as claimed in claim 15, wherein said disk dimension is smaller than a minimum cross-sectional dimension of said displacement space by at least 20%.

17. Milk pump as claimed in claim 16, wherein said disk dimension is smaller than a minimum cross-sectional dimension of said displacement space by at least 30%.

18. Milk pump as claimed in claim 17, wherein said disk dimension is smaller than a minimum cross-sectional dimension of said displacement space by about 35%.

19. The milk pump as claimed in claim 14, wherein said actuator comprises a lever detachably connected to said membrane.

20. Milk pump as claimed in claim 1, wherein said suction unit is pot-shaped.

21. Milk pump as claimed in claim 1, wherein the suction unit has stepped variations in thickness.

* * * * *